(12) United States Patent
Xu et al.

(10) Patent No.: US 6,543,295 B2
(45) Date of Patent: Apr. 8, 2003

(54) HIGH PRESSURE ANVIL AND OPTICAL WINDOW

(75) Inventors: Ji-an Xu, Washington, DC (US); Mao Ho-Kwang, Washington, DC (US)

(73) Assignee: Carnegie Institution of Washington, Washington, DC (US)

(*) Notice: Subject to any disclaimer, the term of this patent is extended or adjusted under 35 U.S.C. 154(b) by 0 days.

(21) Appl. No.: 09/838,562

(22) Filed: Apr. 20, 2001

(65) Prior Publication Data

US 2002/0100309 A1 Aug. 1, 2002

Related U.S. Application Data

(60) Provisional application No. 60/198,754, filed on Apr. 21, 2000.

(51) Int. Cl.⁷ .................................................. G01N 3/00
(52) U.S. Cl. ....................................................... 73/818
(58) Field of Search ........................... 73/818, 819, 820, 73/821, 824, 825, 856, 800

(56) References Cited

U.S. PATENT DOCUMENTS

| | | | | |
|---|---|---|---|---|
| 4,970,396 A | * | 11/1990 | Wong | 250/338.1 |
| 5,113,661 A | * | 5/1992 | Deeks | 62/3.1 |
| 5,594,546 A | * | 1/1997 | Westerfield et al. | 356/246 |
| 5,653,378 A | | 8/1997 | Olson, Jr. et al. | 228/124.1 |
| 5,780,139 A | | 7/1998 | Carter et al. | 428/217 |
| 5,955,735 A | * | 9/1999 | Coleman | 250/336.1 |

OTHER PUBLICATIONS

Amethyst Galleries, 1995 USA Mineral Moissanite.*

* cited by examiner

*Primary Examiner*—Max Noori
(74) *Attorney, Agent, or Firm*—Morgan, Lewis & Bockius LLP

(57) ABSTRACT

The present invention is generally related to high pressure cells used for high pressure and spectroscopic studies. More particularly, the present invention is directed to the use of moissanite in a high pressure cell or a high pressure press as the anvil and/or gasket material. Additionally, the invention relates to the methods of applying pressure to a sample in a high pressure cell and the method for applying pressure to multiple samples in a high pressure cell.

8 Claims, 6 Drawing Sheets

HIGH PRESSURE ANVIL AND OPTICAL WINDOW

DESCRIPTION OF RELATED APPLICATIONS

This application claims benefit of U.S. Provisional Application No. 60/198,754, filed Apr. 21, 2000.

Research in support of the invention described in this application was provided under NSF EAR Grant 9706624.

FIELD OF INVENTION

The present invention is generally related to high pressure cells used for high pressure and spectroscopic studies and applications. More particularly, the present invention is directed to the use of moissanite in high pressure cells and high pressure presses.

BACKGROUND OF THE INVENTION

High pressure cells generate static pressure by squeezing samples between a pair of anvils, which serve as spectroscopic windows. The generation of high pressure for research and development exploratory work has been influenced heavily by apparatus design and strength of materials. Professor Bridgman of Harvard found that he could reach pressures of about 100 Kbar by squeezing thinned samples between flat blocks. This work, starting about 50 years ago, led to the development of the famous Bridgman anvil. Bridgman recognized that if harder materials, such as sintered diamonds, were used for anvils, even higher pressures could be reached. Van Valkenburg and Weir at the National Bureau of Standards (NBS), Washington, D.C., unaware of Bridgman's recommendation, made Bridgman anvils out of single crystal diamond in 1959. This started a revolution in high pressure work. Diamond anvil cells now are ubiquitous devices used throughout the world in high pressure research.

Twenty years later, Mao-Bell high pressure cells achieved pressures up to 500 Kbar utilizing anvils, each of which was a brilliant cut diamond of about one-third carat, the culet being polished to produce a flat of about 0.25 mm$^2$ in area. The Mao-Bell cell was used in the first experimental efforts to break the 50 GPa and 100 GPa barriers. The first pressure calibrations of pressures up to 100, 170, 280, and 550 GPa, in non-hydrostatic conditions, and 80 GPa in quasi-hydrostatic conditions were also achieved using a Mao-Bell cell. In this regard, reference is made to the following publications which are expressly incorporated herein by reference: Bell P. M. et al., "Ultrahigh pressure: beyond 2 megabars and the ruby fluorescence scale", *Science*, 226, 542–544 (1984), and Xu, J. et al., "High pressure ruby and diamond fluorescence: observations at 0.21 to 0.55 terapascal", *Science*, 233, 1404–1406, (1986).

Pressures approaching 360 GPa, equal to the pressure at the center of the earth, have also been reported by Ruoff et al, "Optical Properties of Diamond at Pressures Comparable to the Earth's Center", *Proceedings of the Second International Conference, New Diamond Science and Technology*, Edited by Messier et al, September 23–27, Washington, D.C. Materials Research Society, Pittsburgh, Pa., the disclosure of which is expressly incorporated herein by reference.Experiments up to 300 GPa have become routine; experiments above 400 GPa are far less common, and generally not reproduced.

U.S. Pat. No. 5,295,402 issued to Bovenkirk teaches a method for achieving high pressure in a cell, wherein a sample is placed between a pair of diamond anvils and the anvils compressed. The invention of Bovenkirk involves forming the anvils from one or more of isotopically-pure $^{12}$C or $^{13}$C diamonds.

Diamond-anvil cells ("DAC") are well-known devices, which are used to study materials at high static pressures. In a typical DAC, two brilliant-cut diamonds, each with its culet point truncated to form a planar face, are compressed in opposition against one another. A deformable gasket, consisting of a flat piece of metal foil with a small hole in it, is placed between the opposing diamond faces, with the sample to be studied being contained in the hole in the foil and between the opposing diamond faces. Static pressures on the order of 600 kilobars can be readily obtained by mechanical compression of the diamonds. The primary advantage of the diamond-anvil cell is that the sample can be viewed through the two optically transparent diamonds, thus enabling spectroscopic and other optical studies to be conducted while the sample is compressed.

The construction and operation of conventional diamond anvil high pressure cells is now well known. In this regard, reference is made to the following publications which are expressly incorporated herein by reference: Field, *The Properties of Diamond*, Academic Press, New York City, N.Y. (1979); Manghnani, et al., *High-Pressure Research and Mineral Physics*, Terra Scientific Publishing Company, Tokyo, American Geophysical Union, Washington, D.C. (1987); Homan, "Higher Pressure in Science and Technology", *Mat. Res. Soc. Symp. Proc.*, vol. 22, pp 2939, et seq., Elsevier Science Publishing Company (1984); Vodar, et al., *High Pressure Science and Technology, Proceedings of the VIIth International AIRTAPT Conference*, Le Creusot, France, July 30–Aug. 3, 1979, Pergamon Press, New York, N.Y.; Ruoff et al, "The Closing Diamond Anvil Optical Window in Multimegabar Research", *J. Appl. Phys.*, 69 (9), 6413–6415, May 1, 1991; Mao et al, "Optical Transitions in Diamond at Ultrahigh Pressures", *Nature*, Vol. 351, 721 et seq, Jun. 27, 1991; and Ruoffet al, "Synthetic Diamonds Produce Pressure of 125 GPa (1.25 Mbar)", *J. Mater. Res.*, 2 (5), 614–617, September/October 1987. Conventional opposed diamond anvil cells are fairly uniform in design with variations with respect to improved alignment and alignment adjustment being parameters that the operator can use in designing such cells.

Manghnani, et al., supra, state that improvements may be possible in diamond tip geometry, double beveling, and gasket design in order to achieve higher pressures. These authors further note that stronger diamonds would be desirable and speculate that some advances may be made through the use of synthetic diamonds. In this regard, reference is made to the following publications which are expressly incorporated herein by reference: Bell, P. M., Xu and H. K. Mao, in *Shock Waves in Condensed Matter*, Y. M. Gupta, Editor, Plenum Publishing Co., New York, p. 125 (1986); Hemley, R and Ashcroft, Physics Today, 51, 26, 1998; Hemley, R. et al., "X-ray imaging of stress and strain of diamond, iron and tungsten at megabar pressures", *Science*, 276, 1242–1245, 1997; Hirose, K. et al., *Nature*, 397, 53–56, 1999; Ito, E. et al., *Geophys. Res. Lett.*, 25, 821–824, 1998; Mao, H. K. et al., alibration of the ruby pressure to 800 Kbar under quasi-hydrostatic conditions", *J. Geophysical Research*, 91, 4673–4676, 1986; Pruzan, P. et al., *Europhys. Lett.*, 13, 81, 1995; Xu, J. et al., Raman study on $D_2O$ up to 16.7 GPa in the cubic zirconia anvil cell", J. Ramon Spectroscopy, 27, 823–827, 1996a.

In the past two decades, DACs have pushed high-pressure research to the megabar pressure range, and have revealed new phenomena and new states of matter. The DAC however, also has severe intrinsic limitations that hinder the next level of progress. Perfect diamonds are only available in small sizes, thus restricting the sample chamber to a microscopic volume. For pressures above 30 GPa, the typical 0.3-carat diamond anvil can only hold nanoliter ($10^{-9}$ L) samples. Significantly larger diamonds are impractical as the cost rises as the square of the diamond weight, and perfect diamonds above 30 ct are simply unavailable at any cost. Tungsten carbide and sintered diamond anvils have been used in multianvil (Katsura, T. et al., "Determination of Fe-Mg partitioning between perovskite and magnesiow üstite, *Geophys. Res. Lett.*, 23, 2005–2008 (1996)), and Paris-Edinburgh (Nelmes, R. J. et al., "Multi-site disordered structure of ice VII to 20 GPa", *Phys. Rev. Lett.*, 81, 2719–2722 (1998)) high-pressure apparati to contain microliter ($10^{-6}$ L) or larger samples, but these opaque polycrystalline anvils prohibit spectroscopic studies and are limited to pressures below 30 GPa for carbide and 50 GPa for sintered diamond.

The rarity and expense of diamonds for use in high pressure anvils continues to require that such devices utilize only very small anvils and restricts samples to microscopic size. There have been limited attempts to substitute diamonds with other spectroscopically complementary gem stones. It is now known that with limited pressures of 16.7 GPa for cubic zirconia and 25.8 GPa for sapphire, such substitutes fall well short of the desired pressure levels.

Diamond anvil cells play a major role in high-pressure research. However, it is difficult to study the high-pressure behavior of diamond itself, since the signal from the anvil diamonds seriously interfere with the sample diamond. Such is the case whenever the measured parameters are close to that of a diamond.

Thus a need exists to provide a low cost diamond substitute for use in high pressure anvils. To meet this need the inventors have provided a high pressure cell employing moissanite anvils (and/or moissanite gaskets), which results in improved analysis of larger samples and multiple samples, under extremely high pressure and at much lower cost. Further, the inventors have provided moissanite anvils for use in high pressure window material.

SUMMARY OF THE INVENTION

Accordingly, it is an object and purpose of the present invention to provide a high-pressure anvil cell employing moissanite as the anvil and spectroscopic window material.

Another object of the present invention is to provide a moissanite anvil for use in a high pressure anvil cell at variable temperatures.

Another object of the present invention is to provide a moissanite gasket for use in a high pressure anvil cell.

Another object of the present invention is to provide moissanite as a diamond substitute for industrial applications.

To achieve the foregoing and other objects, and in accordance with the purposes of the present invention, as embodied and broadly described herein, the present invention provides a novel high pressure anvil cell, which accommodates larger samples, and multiple samples, at lower cost than previously thought possible through the use of moissanite anvils and/or moissanite gaskets.

BRIEF DESCRIPTION OF THE DRAWINGS

FIG. 4A shows high-pressure diamond and moissanite anvils capable of being formed with various sizes and shapes. FIG. 4B shows moissanite anvils in a modified Mao-Bell DAC.

DETAILED DESCRIPTION

The inventors have surprisingly found that moissanite (hexagonal SiC) is an ideal high-pressure anvil and spectroscopic window material. While moissanite is known for its brilliance and esthetic appeal, its industrial value, particularly in high pressure anvils, was heretofore not suspected. Moissanite has a Knoop scale hardness of 3000, which is harder than sapphire (2000) and cubic zirconia (1500). Both sapphire and cubic zirconia have been tried as diamond substitutes in high pressure anvils with very limited success. Moissanite's optical transparency and colorlessness are comparable and complementary to diamond, and its index of refraction (2.65–2.69) are higher than diamond (2.45). Large perfect synthetic single-crystal moissanite is available up to the size equivalent of a 300 ct diamond anvil. Such a diamond would not be available at any cost. By scaling up the DAC design, the large moissanite anvils can provide sample volumes 1000 times larger than the standard DAC. The inventors experimented with moissanite anvils in a modified Mao-Bell type DAC. Using the ruby fluorescence spectra measured through the moissanite window for pressure calibration, the moissanite anvils unexpectedly were observed to achieve 52.1 GPa. This surprising result for moissanite anvils clearly entered the high pressure range previously unique only to diamond. The inventor's discovery was the first time static pressures of half a megabar has been reached in a high-pressure device without diamond anvils. Recalling the history of the DAC and the rapid increases in pressure that were achieved after breaking the 50 GPa barrier (Mao, H. K. et al. , "High-pressure physics: the 1-megabar mark on the ruby $R_1$ static pressure scale", *Science*, 191, 851–852 (1976)), significant advances in pressure may be expected with the development of pressure cells optimized for the specific properties of moissanite.

Figure 1:
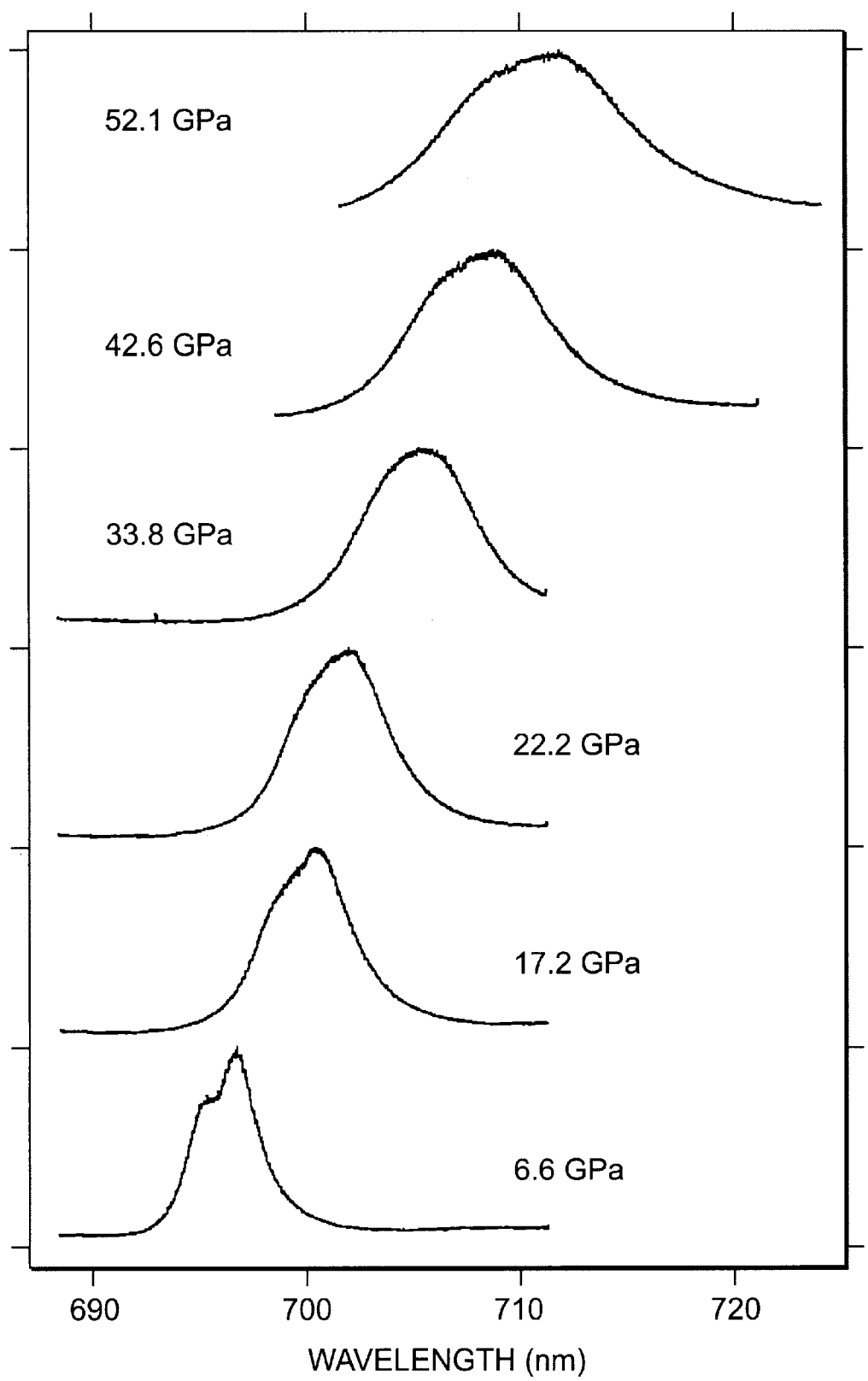
FIG. 1. Ruby fluorescence spectra observed in a Moissanite Anvil Cell ("MAC") up to 52.1 GPa. The experiments were conducted with one moissanite anvil with a 300 µm diameter flat culet opposing a second anvil with a 300 µm, 10° beveled culet and a 100 µm central flat.
Figure 2:
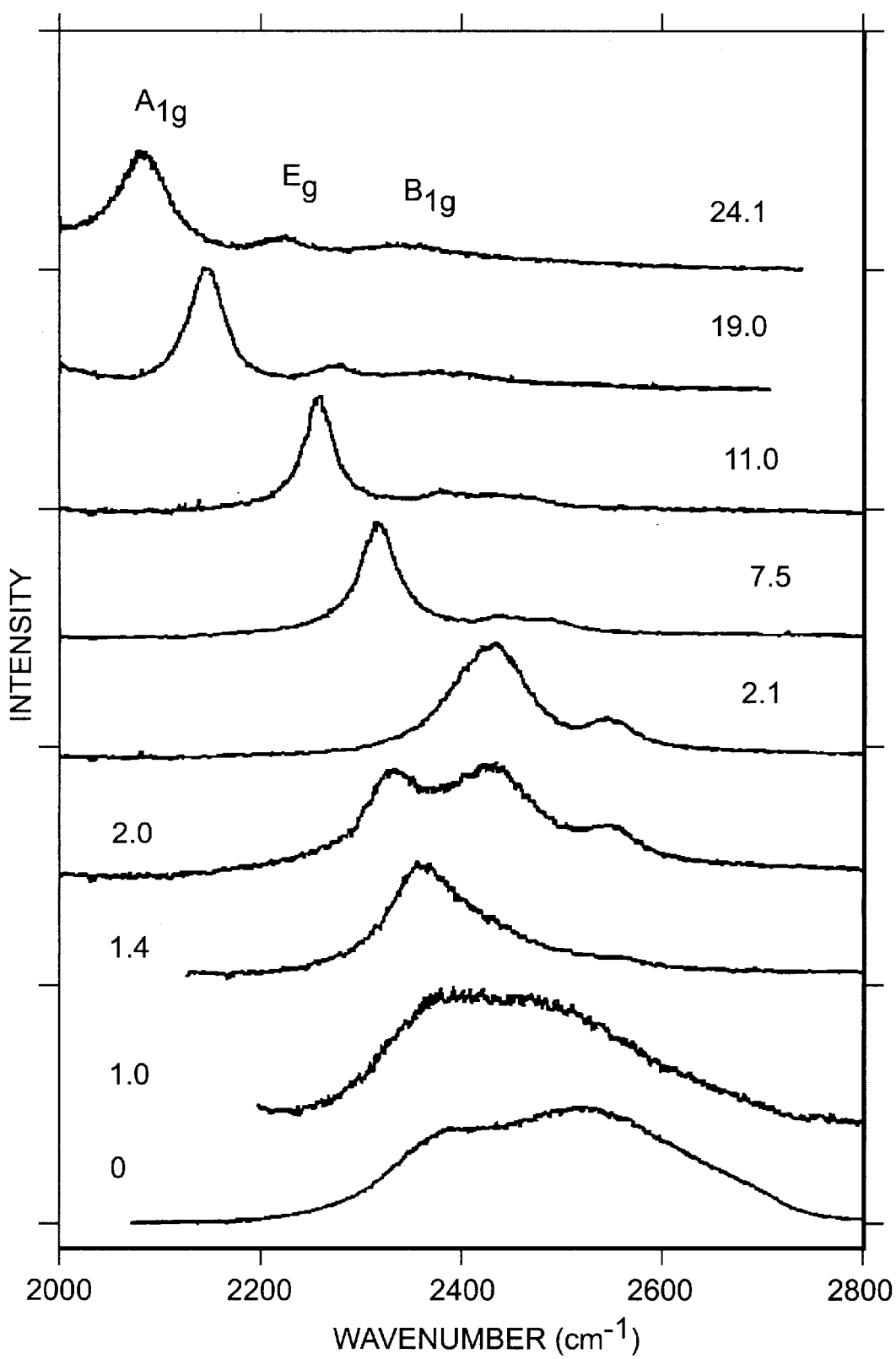
FIG. 2. High-pressure Raman spectra of the liquid (0 and 0.77 GPa), ice VI (1.40 and 1.97 GPa) and ice VII (>2.9 GPa) phases of $D_2O$ measured in a MAC at 298K. The evolution and splitting of $E_g$ and $B_{1g}$ are clearly observed in the region normally obscured by diamond anvils.
Figure 3A:
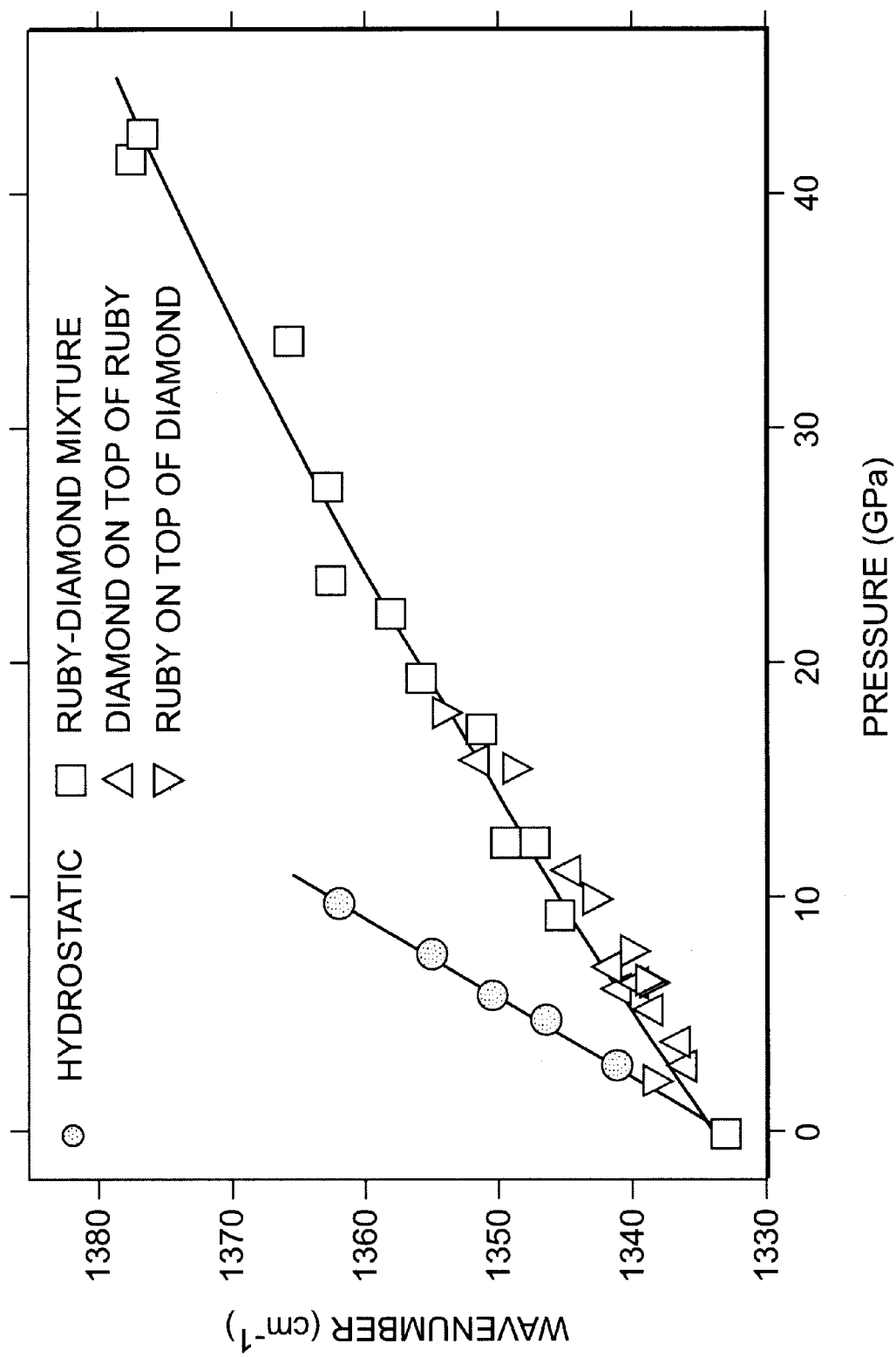
FIGS. 3A and 3B. First order Raman frequency shift of diamond samples as a function of (3A) hydrostatic (ethanol-methanol pressure medium) and (3B) non-hydrostatic (without pressure medium) compressions in a MAC. Three different non-hydrostratic sample configurations yield similar results: open square, intimate mixture of ruby and diamond powder; solid triangles, ruby powder sprinkled on top of compacted diamond powder; open triangles, diamond powder sprinkled on top of compacted ruby powder.
Figure 3B:
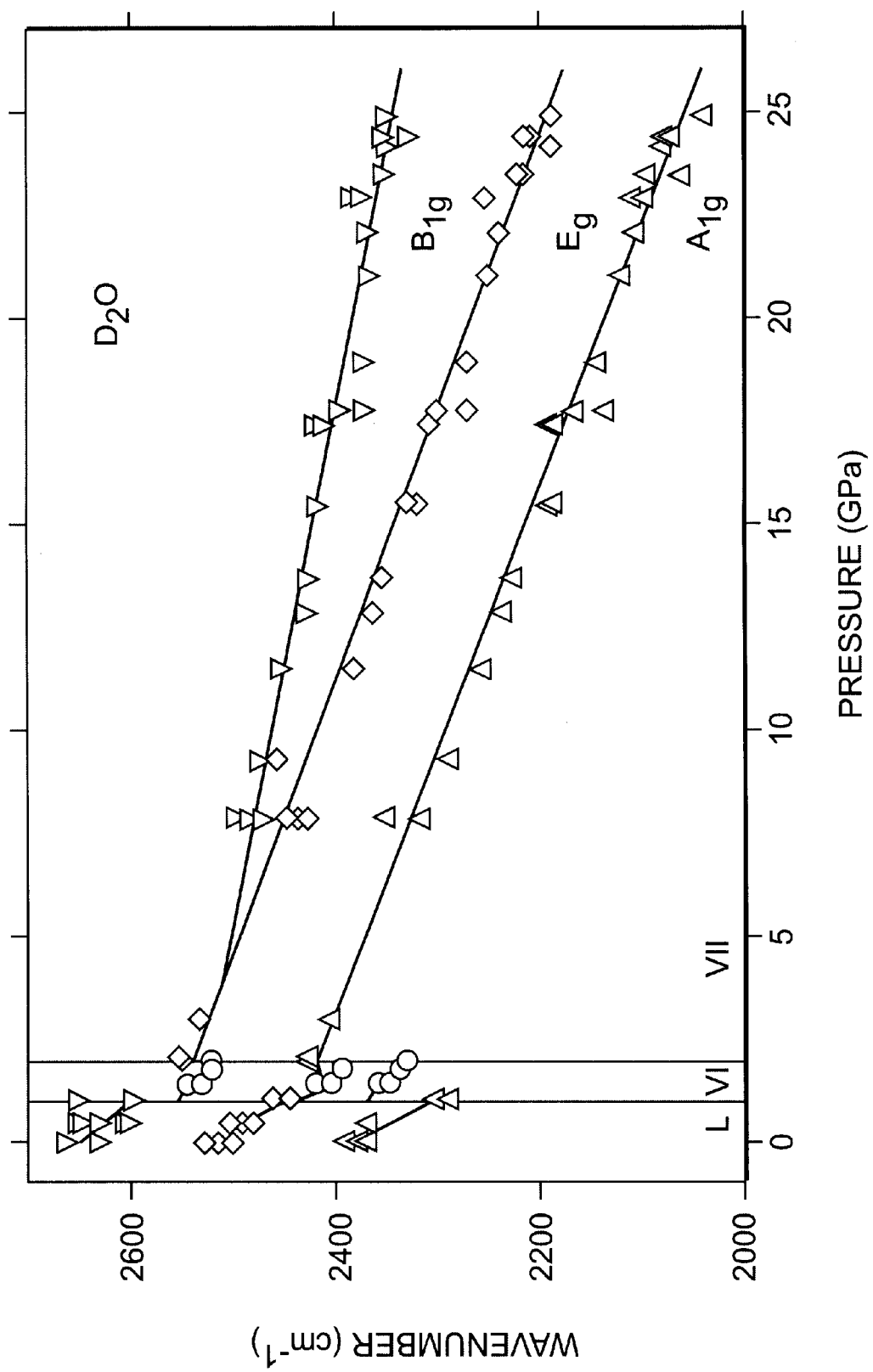

As a clear window for optical spectroscopy, moissanite is comparable and complementary to diamond. Advantageously, the spectra of moissanite does not overlap with the characteristic infrared, Raman, and Brillouin peaks of diamond that often interfere with DAC measurements. For instance, the phonon density of states of diamond that appears as a broad, multi-peak, second-order Raman band in the 2300–2700 $cm^{-1}$ region has been an obstacle for Raman investigation of high-pressure phase transitions and symmetrization of hydrogen bonds in $H_2O$ and $D_2O$ ices in the DAC. This problem, which is inherent in a conventional DAC, is eliminated by using moissanite anvils, which are clear in this region. High quality Raman spectra of high-pressure $D_2O$ are obtained without the background interference found in diamond anvils (See FIG. 2). The inventors have also studied the effect of hydrostatic and nonhydrostatic stresses on the first-order Raman peak ($v_0$=1333 $cm^{-1}$) of diamond which is of considerable interest for understanding the bonding nature of superhard materials. Separation of Raman signals of the diamond sample and the diamond anvils is difficult in the DAC, particularly for pressures below 10 GPa. A C-enriched diamond sample has been used to separate the sample peaks from those of the natural C diamond anvils. The inventors used a MAC to overcome this problem and observed a pressure shift $\partial v/\partial P=2.96\pm0.05$ $cm^{-1}$/GPa for diamond sample compressed in a hydrostatic medium below 10 GPa (See FIG. 3). This is in good agreement with the highest reported value of 2.93 $cm^{-1}$/GPa, measured above 10 GPa in a helium medium in a DAC, indicating that lower values previously reported are derived from spectra contaminated by the signal from diamond anvils or the non-hydrostatic component of the sample. The inventors studied the diamond Raman spectra under non-hydrostatic stress in a MAC and surprisingly observed much smaller peak shifts ($\partial v/\partial P=1.0\pm0.1$ $cm^{-1}$/GPa), approximately one third of the hydrostatic shift (FIG. 3). The triple degeneracy of the $F_{2g}$ zone center phonon is lifted in the randomly orientated diamond grains under non-hydrostatic compression, resulting in a broad peak which would be completely obscured by the diamond anvils but is unmasked in the MAC. Advantageously the present invention, because of the complementary nature of diamond and moissanite, can now be used to explore the entire UV-VIS-IR spectral range from 200 nm to 200 $\mu m$, free of interference from the anvils.

Key properties of moissanite compare favorably to diamond. With high thermal conductivity (500 $WM^{-1}K^{31\ 1}$ at 293 K) and transparency in the near IR, moissanite behaves similarly to diamond in the inventors' test of Nd:YAG laser heating at high pressures. Surprisingly, while diamond requires an inert or reducing atmosphere at temperatures above 900 K to avoid oxidation, the inventors have heated moissanite anvils in air to 1400 K for 36 hours without damage. This discovery demonstrates that the moissanite anvil is surprisingly ideal for high P-T experiments with resistive heating. Like diamond, the moissanite anvil can seal and compress hard-to-contain gases such as hydrogen and helium. The ultrahigh-pressure behaviors of these gases represent some of the most intriguing problems in condensed matter research. In addition, they provide a hydrostatic environment for a whole class of investigations that require strain-free single crystals. Moissanite is a wide-gap insulator suitable for high-pressure electrical conductivity measurements and has no detectable magnetic signal to interfere with high-pressure magnetic measurements. Although moissanite is a stronger x-ray absorber than diamond, the inventors' x-ray diffraction results with the MAC are comparable with that of the DAC at energies above 25 KeV, the main region for high-pressure synchrotron experimentation. Moissanite is more amenable to shaping than diamond, and therefore provides new possibilities for novel anvil designs. Anvils made of moissanite can be cut as cone or facet.

With finite-element calculations, the inventors have discovered that the same maximum pressure can be reached for different sample volumes by a proportional scaling of the dimensions of the anvils, gasket, and sample. The discovery has been verified experimentally with diamond anvils ranging from 0.02 to 2 ct. Single-crystal moissanite is available up to the volume equivalent of a 300 ct diamond anvil (See FIG. 4A). The Figure shows five anvils from the left: (1) 0.3 ct diamond; (2) and (3), conical colorless moissanite anvils with thick girdle; (4) and (5) moissanite anvils shaped similar to the diamond anvils (the bluish color comes from a color center). The largest moissanite anvil (5) on the far right is 25 mm in height, with a volume equivalent to that of a 300 ct diamond anvil. By scaling up the MAC design, the large moissanite anvils will be suitable for compressing microliter samples to over 50 GPa, a previously unheard of possibility. Larger sample sizes will unleash the vast power of many other modem probes such as, for example, neutron diffraction, neutron scattering, inelastic x-ray spectroscopy, x-ray Compton scattering, nuclear magnetic resonance, and ultrasonic interferometry. Such applications have been severely hampered in high-pressure research because of the combined size and pressure constraints of established probes for extreme pressure research, including x-ray diffraction, optical spectroscopy, electrical conductivity, and magnetic susceptibility, to a quality matching studies performed at unconstrained, ambient conditions. The integrated capabilities of versatile measurements, a wide P-T range, hydrostatic conditions, and large sample volume provided by the MAC now open the window to enable high-pressure research to emerge as a major branch of modem science. In this regard, reference is made to the following publications which are expressly incorporated herein by reference: Hemley, R. J. et al., The revealing role of pressure in the condensed matter sciences, *Phys. Today* 51, 26–32 (1998); Hemley, R. J. Mineralogy at a crossroads. *Science* 285, 1026–1027 (1999); McMillan, P. F. et al., Disciplines bound by pressure, *Nature* 391, 539–540 (1998); Struzhkin, V. V. et al., Superconductivity at 10 to 17 K in compressed sulflur. *Nature* 390, 382–384 (1997); Shimizu, K. et al., Superconductivity in oxygen, *Nature* 393, 767–769 (1998); Goncharov, A. F . et al., Raman spectroscopy of dense $H_2O$ and the transition to symmetric hydrogen bonds, *Phys. Rev. Lett.* 83, 1998–2001 (1999); Iota, V. et al., Quartzlike carbon dioxide: An optically nonlinear extended solid at high pressures and temperatures, *Science* 283, 1510–1512 (1999); Zerr, A. et al., Synthesis of cubic silicon nitride, *Nature* 400, 340–342 (1999); Mao, H. K. et al., Design of a diamond-windowed, high-pressure cell for hydrostatic pressures in the range 1 bar to 0.5 Mbar, *Carnegie Inst. Washington Yearb.* 74, 402–405 (1975); Mao, H. K. et al., High-pressure physics: the I-megabar mark on the ruby RI static pressure scale, *Science* 191, 851–852:(1976); Jayararnan, A., The diamond-anvil high-pressure cell, *Sci. Am.* 54–62 (1984); Katsura, T. et al., Detennination of Fe-Mg partitioning between perovskite and magnesiowüstite, *Geophys. Res. Lett.* 23, 2005–2008 (1996); Nelmes, R. J. et al., Loveday, J. S., et al., Multi-site disordered structure of ice VII to 20 GPa, *Phys. Rev. Lett.* 81, 2719–2722 (1998); Xu, J., et al. Ultrahigh pressure in gem anvil cell, *High Pressure Res.* 15, 127–134 (1996); Nassau, K., et al., Synthetic moissanite, a new diamond substitute, *Gems and Gemlogy* 33, 260–275 (1997); Pruzan, P. et al., Raman spectroscopy investigation of ice VII and deuterated ice VII to 40 GPa. Disorder in ice VII, *Europhys. Lett.* 13, 81–87 (1990); Goncharov, A. F . et al., Compression of ice to 210 GPa: Evidence for a symmetric hydrogen bonded phase, *Science* 273, 218–220 (1996); Hanfland, M. et al., Raman study of diamond anvils under stress. *J. Appl. Phys.* 57, 2752–2756 (1985); Aleksandrov, V. et al., Diamond at high pressures: Raman scattering of light, equation of state, and high-pressure scale, *Sov. Phys. JETP* 66, 384–390 (1987); Schiferl, D. et al., The diamond 13C/12C isotope Raman pressure sensor system for high-temperature/pressure diamond-anvil cells with reactive samples, *J. Appl. Phys.* 82, 3258–3265 (1997); Fei, Y. et al., In situ determination of the NiAs phase of FeO at high pressure and high temperature, *Science* 266, 1678–1680 (1994); Mao, H. K. et al., Ultrahigh-pressure transitions in solid hydrogen, *Rev. Mod. Phys.* 66, 671–692 (1994); Johnson, K. A. et al., Structure arid bandgap closure in dense hydrogen, *Nature* 403, 632–635 (2000); Celliers, P. M. et al., Shock-induced transformation of liquid deuterium into a metallic fluid, *Phys. Rev. Lett.* 84, 5564–5567 (2000); Loubeyre, P. et al., X-ray diffraction and equation of state of hydrogen at megabar pressures, *Nature* 383, 702–704 (1996); Merkel, S. et al., Finite element modeling of diamond deformation at multimegabar pressures, *Appl. Phys. Lett.* 74, 656–658 (1999); Link, P. et al., Ferromagnetic mixed-valence and Kondo-lattice state in TmTe at high pressure, *Phys. Rev. Lett.* 80, 173–176 (1998); Ruocco, G. et al., Equivalence of the sound velocity in water and ice at mesoscopic wavelengths. *Nature* 379,521–523 (1996); Lee, S. H. et al., Improved NMR resonator for diamond anvil cells, *Rev. Sci. Instrum.* 63, 3674–3676 (1992); Li, B. et al., Elastic moduli of wadsleyite ($\beta$-$Mg_2SiO_4$) to 7 gigapascals and 873 kelvin, *Science* 281,675–677 (1998).

Figure 4A:
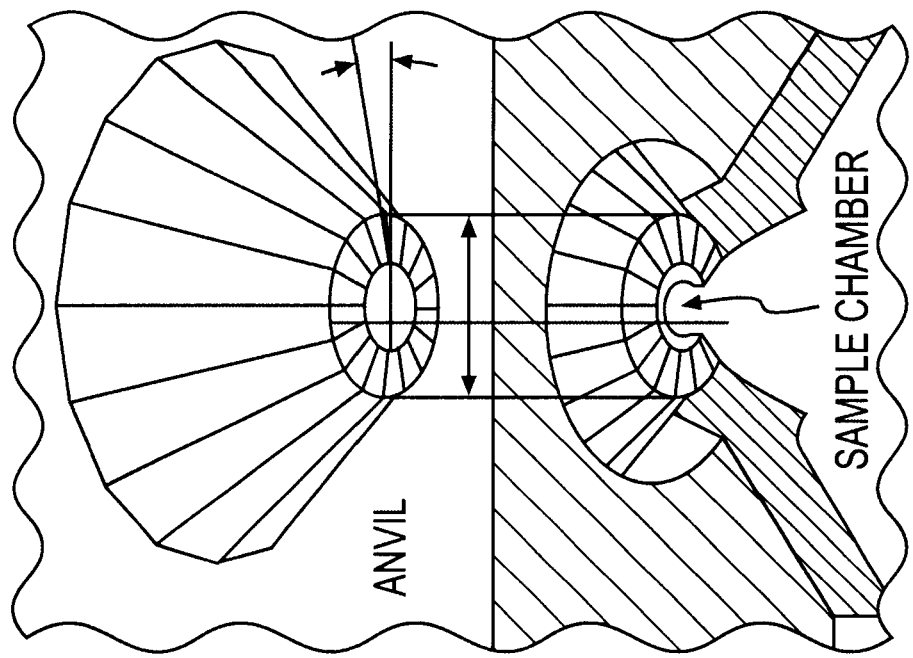
FIGS. 4A–B.
Figure 4B:
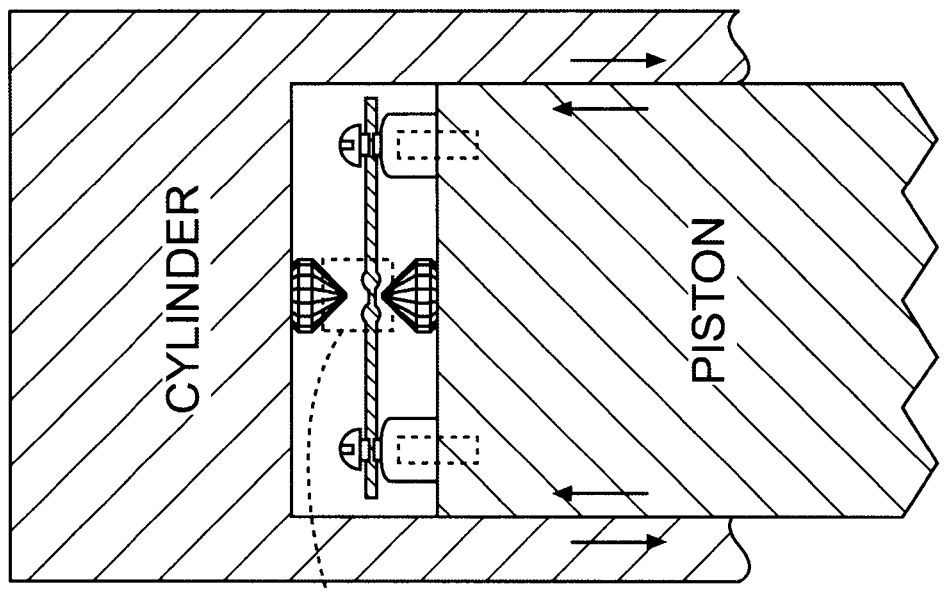
Figure 5:
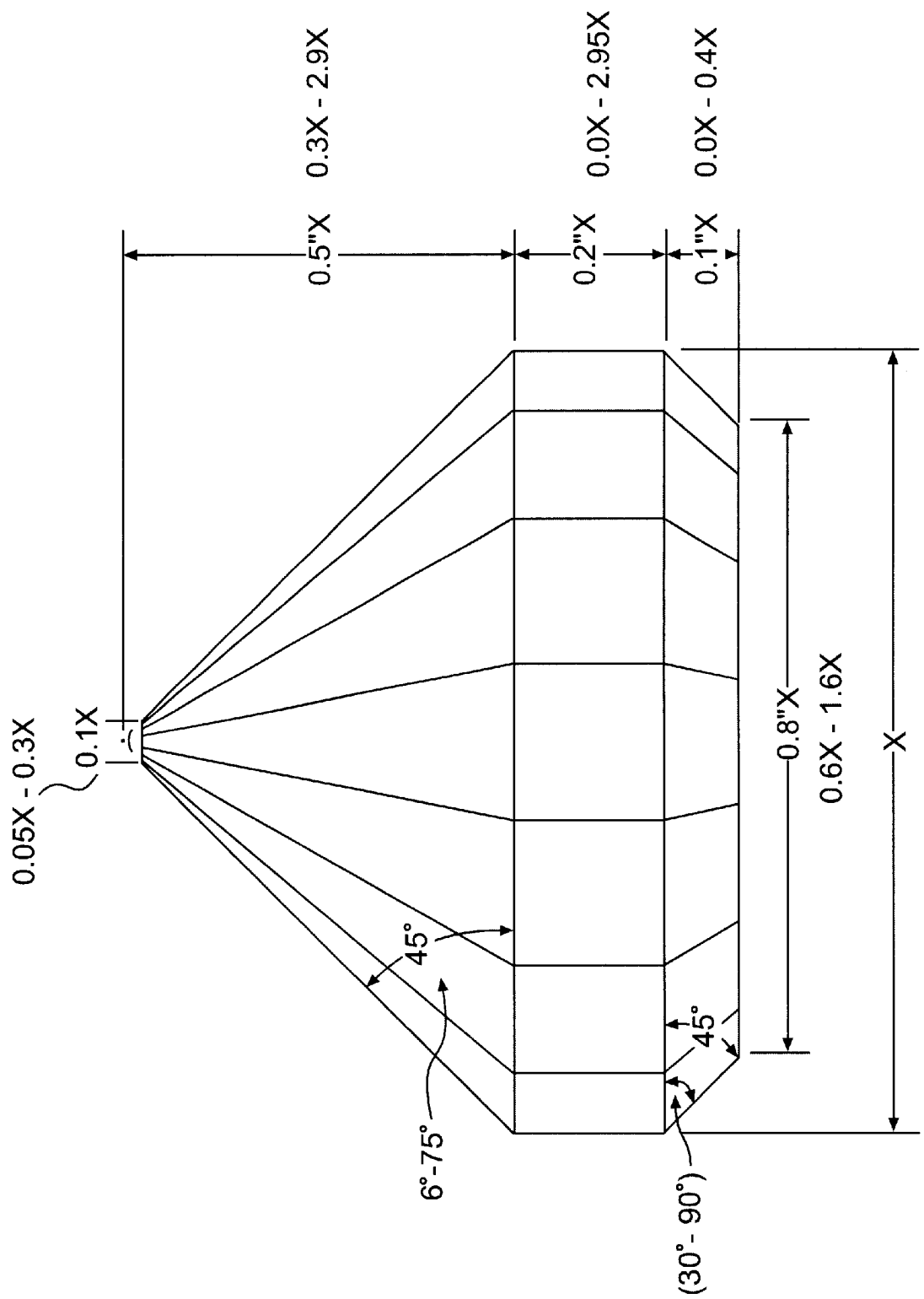
FIG. 5. Diagram of an anvil with proportions and angles of cut.

Unlike traditional (8- or 16-side) brilliant-cut or other similar cut stones generally in use with diamond anvils, the culet of a moissanite anvil can be cut to a near circle. Performance will vary with differently cut anvils. Also, unlike diamond anvils which are extremely limited in size, it is possible to fabricate large size moissanite anvil devices (for example, in the size of 1-inch anvils), since good quality large crystals can be grown by synthetic techniques. Non-limiting examples of moissanite anvils with different cutting and sizes are shown in FIG. 4A. FIG. 4B shows moissanite anvil replacing diamonds in a modified Mao-Bell DAC. The volume of the moissanite anvils in the DAC is equivalent to an 8.0 ct diamond.

The dimensions of a moissanite anvil will vary depending on the combination of anvils and gasket proportions desired. The moissanite anvils can generally follow the proportions given in Table 1. However, the moissanite anvil can also be beveled at the culet, so as to have a bevel angel in the order of about 10°. There are other proportions and cuts that will vary the performance of the anvil and will be known to those skilled in the art. A particular advantage of moissanite anvils over conventional diamond anvils is the wider range of possible cuts, the variety of possible proportionate dimensions, and the comparatively limitless size of moissanite anvils, and therefore the potential for use of larger samples with moissanite anvils.

TABLE 1

Proportional dimensions (ratios) of a Moissanite anvil:

| | |
|---|---|
| Girdle Diameter | X |
| Table Width | 0.6X–1.6X |
| Crown Height | 0.0X–0.4X |
| Girdle Thickness | 0.0X–2.95X |
| Pavilion Depth | 0.3X–2.9X |
| Culet Diameter | 0.01X–0.75X |
| Crown Angle | 30°–90° |
| Pavilion Angle | 6°–75° |
| Girdle Angle | −5°–5° |

The characteristics of moissanite also make it surprisingly functional as gasket material. Samples can be studied for properties that best utilize the optical, chemical, and physical qualities of moissanite where moissanite is employed as a gasket. These properties are shown in Table 2. Multiple sample chambers in the form of wells or holes can be created in or on the gasket made of polycrystalline moissanite or other materials. Moissanite gaskets can also be indented during the manufacturing process to form sample chambers rather than opened with drilled holes as in conventional gaskets. The methods by which sample chambers are created can include drilling, etching and other methods known to those skilled in the art. Non-limiting examples are shown in FIG. 4A.

TABLE 2

Physical, Chemical, biological, or electrical characteristics of Moissanite:

| | |
|---|---|
| Chemical composition | SiC |
| Crystal structure | Hexagonal |
| Density | 3.217 g/cm$^3$ |
| Hardness (Knoop Scale) | 3000 |
| Hardness (Mohr Scale) | 9.25 |
| Bulk modulus (GPa) | 267–335 GPa |
| Melting point | 2700° C. |
| Thermal conductivity (at 293K) | 140–500 W/m-K |
| Thermal inertia | 1.6–4.8 cal/cm-K |
| Refractive index, n | 2.65–2.69 |
| Highest P | 52.1 GPa |

Multiple sample chambers can be labeled with indicia by which distinct samples can be identified. This indicia can be etched, burned or otherwise marked by methods known to those who are skilled in the art of etching and indicia application, such that the indicia applied to the gasket is proximate to the sample chambers thereby allowing unobstructed, positive identification of the sample chambers. The indicia can be created such that identification of the sample chambers can be done by automated means. Such indicia can include a bar code system or other scanable system that can be read by a low power laser scanner and computer.

Ideally, gaskets having single or multiple sample chambers can be loaded by mechanical or by automated means. Dampening devices associated with manipulators, that increase the control when handling microscopic samples, may be used to place distinct samples into separate chambers with great accuracy. Automated means may also be used to load multiple samples into separate chambers simultaneously. Further, with the increase in size of a MAC, current manual techniques of externally applied pressure may not be sufficient. In larger MACs, augmented mechanical means such as electrically driven pressure, hydraulically driven pressure, or any other power-multiplying method by which pressure can be exerted on an anvil beyond that capable by hand, might be used.

Moissanite anvils are capable of being used as a substitute for any anvil conventionally used in a high pressure press. Moissanite anvils can be utilized in industrial applications at pressures below about 52.1 GPa and, if required, at high temperatures. Varying the cut of the moissanite anvil can increase the pressure at which such anvils are effective. These applications include substituting moissanite as the anvil material in the high pressure production of diamonds, multiple clustered anvil arrays designed to subject materials to high pressure, and any other use of a high pressure press for industrial applications known to those skilled in the art.

With the advantages of lower cost, larger size, and superior optical properties, moissanite has been shown to provide a suprisingly superior substitute for diamond as the high-pressure anvils and windows. High pressure anvil employing moissanite will revolutionize the research field and greatly expand the use of high pressure anvils by finally providing anvils capable of analyzing much larger samples than heretofore believed possible.

What is claimed is:

1. A high pressure cell for studying a sample of a material at high static pressure, wherein said cell comprises:

first and second moissanite anvils each having a beveled surface between a side surface and culet surface, wherein each culet surface is circular and configured as a spectroscopic window for examining the sample;

a gasket positioned between said anvils such that the beveled surface and the culet surface of each anvil are in contact with the gasket;

a pocket in the gasket for receiving the sample positioned between the culet surfaces of the first and second moissanite anvils.

2. A cell according to claim 1, wherein said anvils are a strain-free single crystal.

3. A cell according to claim 1, wherein said anvils have dimensional proportions for a given Girdle diameter, X, as follows: Table width 0.6X to 1.6X; Crown height 0.0X to 2.9X; Girdle thickness 0.0X to 2.95X; Pavilion depth 0.05X to 2.9X; Culet diameter 0.01X to 0.75X; Crown angle 30° to 90°; Pavilion angle 6° to 75°; and Girdle angle −5° to 5°.

4. A cell according to claim 1, wherein a beveled surface of at least one anvil is at angle of about 1° to 30° with respect to the culet surface of the at least one anvil.

5. A high pressure cell for studying a sample of a material at high static pressure, wherein said cell comprises:

first and second moissanite anvils each having a beveled surface between a side surface and culet surface, wherein each culet surface is configured as a spectroscopic window for examining the sample and a beveled surface of at least one anvil is at an angle of about 1°–30° with respect to the culet surface of the at least one anvil;

a gasket positioned between said anvils such that the side surface, beveled surface and the culet surface of at least one anvil are in contact with the gasket;

a pocket in the gasket for receiving the sample positioned between the culet surfaces of the first and second moissanite anvils.

6. A cell according to claim 5, wherein said anvils are a strain-free single crystal.

7. A cell according to claim 5, wherein said anvils have dimensional proportions for a given Girdle diameter, X, as follows: Table width 0.6X to 1.6X; Crown height 0.0X to 2.9X; Girdle thickness 0.0X to 2.95X; Pavilion depth 0.05X to 2.9X; Culet diameter 0.0X to 0.75X; Crown angle 30° to 90°; Pavilion angle 6° to 75°; and Girdle angle −5° to 5°.

8. A cell according to claim 5, wherein said culet surface is circular.

* * * * *